United States Patent
Tacke et al.

(10) Patent No.: US 6,821,922 B1
(45) Date of Patent: Nov. 23, 2004

(54) SUPPORTED CATALYST FOR THE PRODUCTION OF VINYL ACETATE MONOMER

(75) Inventors: Thomas Tacke, Paducah, KY (US); Helmfried Krause, Rodenbach (DE); Hermanus G. J. Lansink Rotgerink, Mömbris-Mensengesäß (DE); Francis Daly, Murray, KY (US); Martin Reisinger, Haingründau (DE); Helmut Mangold, Rodenbach (DE)

(73) Assignee: Degussa - HULS AG (DE)

( * ) Notice: Subject to any disclaimer, the term of this patent is extended or adjusted under 35 U.S.C. 154(b) by 0 days.

(21) Appl. No.: 09/404,537

(22) Filed: Sep. 24, 1999

(30) Foreign Application Priority Data

Sep. 24, 1998 (DE) .......................... 198 43 693

(51) Int. Cl.$^7$ .......................... B01J 23/58; B01J 21/08; B01J 21/12; B01J 21/14; B01J 23/40
(52) U.S. Cl. .................. 502/330; 502/242; 502/243; 502/253; 502/262; 502/326; 502/328; 502/339; 502/340; 502/344; 502/407; 502/439
(58) Field of Search .................. 502/326, 328, 502/330, 339, 340, 344, 439, 242, 243, 253, 262, 407

(56) References Cited

U.S. PATENT DOCUMENTS

| | | | | |
|---|---|---|---|---|
| 4,119,567 A | * | 10/1978 | Bartsch .................. 525/430 |
| 4,902,823 A | | 2/1990 | Wunder et al. | |
| 5,185,308 A | * | 2/1993 | Bartley et al. .......... 502/170 |
| 5,250,487 A | | 10/1993 | Wirtz et al. | |
| 5,292,931 A | | 3/1994 | Wirtz et al. | |
| 5,407,886 A | * | 4/1995 | Schneider et al. ......... 502/244 |
| 5,559,071 A | * | 9/1996 | Abel et al. ............... 502/326 |
| 5,571,771 A | * | 11/1996 | Abel et al. ............... 502/330 |
| 5,591,688 A | * | 1/1997 | Blum et al. .............. 502/330 |
| 5,622,908 A | | 4/1997 | Abel et al. | |
| 5,672,734 A | | 9/1997 | Abel et al. | |
| 5,674,800 A | * | 10/1997 | Abel et al. ............... 502/326 |
| 5,808,136 A | | 9/1998 | Tacke et al. | |
| 5,854,171 A | * | 12/1998 | Nicolau et al. .......... 502/330 |
| 5,935,897 A | * | 8/1999 | Trubenbach et al. ... 502/527.14 |
| 5,935,898 A | * | 8/1999 | Trubenbach et al. ... 502/527.14 |
| 5,968,860 A | * | 10/1999 | Herzog ...................... 502/5 |
| 5,972,824 A | * | 10/1999 | Herzog et al. ............ 502/160 |
| 5,998,659 A | * | 12/1999 | Abel .......................... 560/245 |
| 6,034,030 A | * | 3/2000 | Nicolau et al. .......... 502/326 |
| 6,057,260 A | * | 5/2000 | Nicolau et al. .......... 502/331 |

FOREIGN PATENT DOCUMENTS

| | | |
|---|---|---|
| DE | 21 00 778 B2 | 8/1972 |
| EP | 0 330 853 A2 | 9/1989 |
| EP | 0 403 950 A1 | 12/1990 |
| EP | 0 519 435 A1 | 12/1992 |
| EP | 0 634 208 A1 | 7/1994 |
| EP | 0 723 810 A1 | 7/1995 |
| EP | 0 807 615 A | 11/1997 |

* cited by examiner

*Primary Examiner*—Cam N. Nguyen
(74) *Attorney, Agent, or Firm*—Smith, Gambrell & Russell, LLP

(57) ABSTRACT

Moldings based on pyrogenically produced mixed oxide having the following physicochemical parameters:

| | |
|---|---|
| External diameter | 0.8–25 mm |
| BET surface area | 5–400 m$^2$/g |
| Pore Volume | 0.2–1.8 ml/g |
| Fracture strength | 5 to 350 N |
| Composition | At least two oxides selected from the group $SiO_2$, $Al_2O_3$, $TiO_2$ and $ZrO_2$ in any desired combination but with the exception of $SiO_2/Al_2O_3$ mixed oxides, in which > 75 wt. % of $SiO_2$ is present. |
| Other constituents | <1 wt. % |
| Bulk density | 250–1500 g/l, | are produced by homogenizing pyrogenically produced mixed oxide as desired with one or more compounds from the group methylcellulose, methylhydroxyethylcellulose, wax, polyethylene glycol, magnesium stearate and/or aluminium stearate with addition of water, drying the product at a temperature of 70–150° C., optionally comminuting the dried product to yield a powder, optionally compressing the powder to yield moldings and performing heat treatment for a period of 0.5 to 10 hours at a temperature of 400 ° to 1200° C. These moldings are then doped with suitable catalytically active components for the production of vinyl acetate monomer using a gas phase process.

8 Claims, No Drawings

SUPPORTED CATALYST FOR THE PRODUCTION OF VINYL ACETATE MONOMER

CROSS-REFERENCE TO RELATED APPLICATION

This application is based on German Application DE 198 43 693.9, filed Sep. 24, 1998, which disclosure is incorporated herein by reference.

FIELD OF THE INVENTION

This invention relates to a supported catalyst based on pyrogenically produced mixed oxide, which catalyst is in particular suitable for the production of vinyl acetate monomer (VAM).

BACKGROUND OF THE INVENTION

Pyrogenically produced oxides are distinguished by extreme fineness and a correspondingly elevated specific surface area, very high purity, spherical particle shape and the absence of pores. Due to these properties, there is increasing interest in pyrogenically produced oxides as supports for catalysts (D. Koth, H. Ferch, Chem. Ing. Techn. 52, 628 (1980)). In some cases, pyrogenic oxides are also used as a catalyst.

Since pyrogenically produced oxides are particularly finely divided, shaping them into catalyst supports or catalysts occasions some difficulties.

It is known from DE-B 21 00 778 to use pellets based on pyrogenically produced silicon dioxides as catalyst supports in the production of vinyl acetate monomer.

Further production processes for the production of vinyl acetate monomer are known from the documents DE 16 68 088, U.S. Pat. No. 4,048,096, EP-A 0 519 435, EP-A 0 634 208, EP-A 0 723 810, EP-A 0 634 209, EP-A 0 632 214, EP-A 0 654 301 and EP-A 0 723 810. These documents also describe processes for the production of supported catalysts. Depending upon the embodiment, supported catalysts are obtained which have a homogeneous distribution of noble metal over the support cross-section and have a more or less pronounced shell profile.

EP-A 0 723 810 describes a pretreatment method for catalyst supports for the production of vinyl acetate monomer with elements of groups IA, IIA, IIIA and IVB of the periodic system.

The disadvantage of these prior art processes is that they give rise to catalysts which result in an unfavorable relationship of selectivity and activity in the production of vinyl acetate monomer.

It is known to produce pyrogenic mixed oxides by simultaneously reacting at least two different metals in the form of volatile metal compounds, for example chlorides, in a $H_2/O_2$ flame. One example of such an oxide is the $SiO_2/Al_2O_3$ mixed oxide, which is produced by Degussa-Hüls AG, Germany, and sold under the tradename AEROSIL® MOX 170. When producing AEROSIL® MOX 170, a mixture of $SiCl_4$ and $AlCl_3$ is directly hydrolyzed in a flame. Corresponding silanes, such as for example methyltrichlorosilane, trichlorosilanes etc. may also be used as a raw material instead of or in addition to the chlorides. (Degussa Technical Bulletin Pigments, No. 11: Basic Characteristics of AEROSIL®, pages 37 and 11–12; AT-A 195 893; DE-A 952 891; DE-A 25 33 925; DE-A 27 02 896).

SUMMARY OF THE INVENTION

The present invention uses novel moldings based on pyrogenically produced mixed oxide having the following physicochemical parameters:

| | |
|---|---|
| External diameter | 0.8–25 mm |
| BET surface area | 5–400 m$^2$/g |
| Pore volume | 0.2–1.8 ml/g |
| Fracture strength | 5 to 350 N |
| Composition | At least two members selected from the group $SiO_2$, $Al_2O_3$, $TiO_2$ and $ZrO_2$ in any desired combination, but with the exception of $SiO_2/Al_2O_3$ mixed oxides, in which >75 wt. % of $SiO_2$ is present. |
| Other constituents | <1 wt. % |
| Bulk density | 250–1500 g/l |

The moldings according to the invention may be present as extruded moldings, extrudates or tablets. They may assume the form of cylinders, cylinders having rounded end faces, spheres, rings, wagon wheels, miniliths or other shapes conventional for fixed bed catalysts.

The moldings according to the invention based on pyrogenically produced mixed oxide having the following physicochemical parameters:

| | |
|---|---|
| External diameter | 0.8–25 mm |
| BET surface area | 5–400 m$^2$/g |
| Pore volume | 0.2–1.8 ml/g |
| Fracture strength | 5–350 N |
| Composition | At least two members selected from the group $SiO_2$, $Al_2O_3$, $TiO_2$ and $ZrO_2$ in any desired combination, but with the exception of $SiO_2/Al_2O_3$ mixed oxides, in which >75 wt. % of $SiO_2$ is present. |
| Other constituents | <1 wt. % |
| Bulk density | 250–1500 g/l, | may be produced by homogenizing pyrogenically produced mixed oxide as desired with one or more compounds selected from the group methylcellulose, methylhydroxyethylcellulose, wax, magnesium stearate, aluminium stearate and polyethylene glycol with addition of water, drying the product at a temperature of 70°–150° C., optionally comminuting it to yield a powder, compressing the powder to yield moldings and performing heat treatment for a period of 0.5 to 10 hours at a temperature of 400° to 1200° C.

The moldings according to the invention may be produced in stamping presses, eccentric presses, isostatic presses, extrusion presses, rotary presses or compactors.

Before pressing, one particular embodiment of the invention may exhibit the following composition:

| | |
|---|---|
| mixed oxide | 50–90 wt. % |
| methylhydroxyethylcellulose | 0.1–20 wt. %, preferably 5–15 wt. % |
| wax | 0.1–15%, preferably 5–12 wt. % |
| polyethylene glycol | 0.1–15%, preferably 5–10 wt. % |

Fracture strength, specific total surface area and pore volume may be adjusted to a certain extent by varying the quantities of starting materials and the compression pressure.

Alternatively, the moldings according to the invention based on pyrogenically produced mixed oxide having the following physicochemical parameters:

| | |
|---|---|
| External diameter | 0.8–25 mm |
| BET surface area | 5–400 m$^2$/g |
| Pore volume | 0.2–1.8 ml/g |
| Fraction strength | 5–350 N |
| Composition | At least two members selected from the group SiO$_2$, Al$_2$O$_3$, TiO$_2$ and ZrO$_2$ in any desired combination but with the exception of SiO$_2$/Al$_2$O$_3$ mixed oxides, in which >75 wt. % of SiO$_2$ is present. |
| Other constituents | <1 wt. % |
| Bulk density | 250–1500 g/l, | may be produced by homogenizing pyrogenically produced mixed oxide as desired with one or more compounds from the group methylcellulose, methylhydroxyethylcellulose, wax, magnesium stearate, aluminium stearate and/or polyethylene glycol with addition of water, subjecting the product to a kneading and shaping process, extruding it, optionally chopping the extrudates to the desired length by means of a chopping device, drying the product at a temperature of 70°–150° C. and performing heat treatment for a period of 0.5 to 10 hours at a temperature of 400° to 1200° C.

Any mixers or mills which permit good homogenization, such as for example blade mixers, fluidized bed mixers, centrifugal mixers or air-swept mixers, are suitable for performing the process according to the invention. Particularly suitable mixers are those with which the material being mixed may additionally be compacted, such as for example plough bar mixers, pan mills or ball mills. Mixing and kneading may, however, also proceed directly in an extruder. The extrudates may also be produced in single or twin-screw extruders, extrusion presses as well as in compactors.

After homogenization, the product may be largely dried at 70°–150° C., such that, after an optional comminution operation, a pourable powder is obtained.

The moldings according to the invention may be used either directly as a catalyst or as a catalyst support.

One object of the present invention is to provide a supported catalyst which, with identical or improved selectivity, exhibits greater activity than known catalysts.

The present invention accordingly provides a supported catalyst which contains palladium and/or the compounds and alkali metal compounds thereof, as well as additionally gold and/or the compounds thereof (Pd/alkali metal/Au system) or cadmium and/or the compounds thereof (Pd/alkali metal/Cd system) or barium and/or the compounds thereof (Pd/alkali metal/Ba system) or palladium, alkali metal compounds and mixtures of gold and/or cadmium and/or barium as the catalytically active components on a support or molding, characterized in that the support is based on pyrogenically produced mixed oxide having the following physicochemical parameters:

| | |
|---|---|
| External diameter | 0.8–25 mm |
| BET surface area | 5–400 m$^2$/g |
| Pore volume | 0.2–1.8 ml/g |
| Fracture strength | 5–350 N |
| Composition | At least two members selected from the group SiO$_2$, Al$_2$O$_3$, TiO$_2$ and ZrO$_2$ in any desired combination but with the exception of SiO$_2$/Al$_2$O$_3$ mixed oxides in which >75 wt. % of SiO$_2$ is present. |
| Other constituents | <1 wt. % |
| Bulk density | 250–1500 g/l |

Potassium compounds, such as for example potassium acetate, are preferred as the alkali metal compounds.

The catalytically active components may be present in the following systems:
Pd/Au/alkali metal compounds
Pd/Cd/alkali metal compounds
Pd/Ba/alkali metal compounds.

The supported catalysts according to the invention are in particular used for the production of vinyl acetate monomer. To this end, ethylene, acetic acid and molecular oxygen or air are reacted in the gas phase, optionally with the addition of inert gases, at temperatures of between 100° and 250° C. and at standard or elevated pressure in the presence of the supported catalyst according to the invention. These catalysts may, however, also in principle be used for acetoxylating olefins, such as for example propylene.

The present invention also provides a process for the production of the supported catalyst according to the invention by, in a suitable order, applying the Pd, Au, Cd, Ba metal compounds by impregnation, spraying, vapor deposition, immersion or precipitation, optionally reducing the reducible metal compounds applied onto the support, washing to remove any optionally present chloride content, performing impregnation with alkali metal acetates or alkali metal compounds which are entirely or partially converted into alkali metal acetates under the reaction conditions for the production of vinyl acetate monomer, wherein the support is a molding based on pyrogenically produced mixed oxide.

The present invention also provides a process for the production of the supported catalyst according to the invention by impregnating the support with a basic solution and a solution containing gold and palladium salts, wherein impregnation proceeds simultaneously or in succession, with or without intermediate drying, washing the support to remove any optionally present chloride content and, before or after washing, reducing the insoluble compounds precipitated on the support, drying the resultant catalyst precursor, and performing impregnation with alkali metal acetates or alkali metal compounds which are entirely or partially converted into alkali metal acetates under the reaction conditions for the production of vinyl acetate monomer, wherein the support is a molding based on pyrogenically produced mixed oxide.

The supported catalysts according to the invention may be used for the production of unsaturated esters from olefins, acids and oxygen in the gas phase.

The catalysts according to the invention of the Pd/alkali metal/Au system may be obtained by impregnating the support with a basic solution and a solution containing gold and palladium salts, wherein the impregnation steps may proceed simultaneously or in succession, with or without intermediate drying. The support may then be washed to remove any optionally present chloride content. The insoluble noble metal compounds precipitated on the support may be reduced before or after washing. The catalyst precursor obtained in this manner may be dried and, in order to activate the catalyst, be impregnated with alkali metal acetates or alkali metal compounds which are entirely or partially converted into alkali metal acetates under the reaction conditions for the production of vinyl acetate monomer. In general, the noble metals in Pd/Au catalysts may be present in the form of a shell on the support.

In the case of Pd/alkali metal/Ba catalysts, the metal salts may be applied by impregnation, spraying, vapor deposition, immersion or precipitation (EP 0 519 436). The same methods are known for Pd/alkali metal/Cd catalysts (U.S. Pat. No. 4,902,823, U.S. Pat. No. 3,393,199, U.S. Pat. No. 4,668,819).

Depending upon the catalyst system, the supported catalyst may be reduced.

The catalyst may be reduced in the aqueous phase or in the gas phase. Formaldehyde or hydrazine are, for example, suitable for reduction in the aqueous phase. Reduction in the gas phase may be performed with hydrogen or forming gas (95 vol. % $N_2$+5 vol. % $H_2$), ethylene or nitrogen-diluted ethylene. According to EP 0 634 209, reduction with hydrogen proceeds at temperatures of between 40° and 260° C., preferably between 70° and 200° C. According to EP-A 0 723 810, reduction with forming gas (95 vol. % $N_2$ and 5 vol. % $H_2$) proceeds at temperatures of between 300° and 550° C., preferably between 350° and 500° C. Frequently, however, the catalyst is reduced directly in the production reactor with ethylene only once it has been activated with alkali metal acetate.

In the production process, the catalyst is exposed only slowly to the reactant. Catalyst activity increases during this start-up phase and does not usually reach its final level until some days or weeks have elapsed.

What is of significance is that the catalyst supports retain their mechanical strength under the reaction conditions of the catalytic process, in particular on exposure to acetic acid.

The supported catalyst according to the invention achieves excellent selectivity at elevated activity.

Production of supported catalysts of the Pd/alkali metal/Au system on the support (molding) according to the invention is described in greater detail below.

The moldings according to the invention based on pyrogenically produced mixed oxide may be impregnated with a solution containing palladium and gold. The moldings according to the invention may be impregnated with a basic solution, which may contain one or more basic compounds, simultaneously with the solution containing noble metal or in any desired order. The purpose of the basic compound or compounds is to convert the palladium and gold into the hydroxides thereof.

The compounds in the basic solution may consist of alkali metal hydroxides, alkali metal bicarbonates, alkali metal carbonates, alkali metal silicates or mixtures of these substances. Potassium hydroxide and/or sodium hydroxide may preferably be used.

The solution containing noble metal may be produced by using, for example, palladium chloride, sodium or potassium palladium chloride or palladium nitrate, as the palladium salts. Gold(III) chloride and tetrachloroauric(III) acid are suitable as the gold salts. Potassium palladium chloride, sodium palladium chloride and/or tetrachloroauric acid are preferably used.

Impregnation of the moldings according to the invention with the basic solution influences the deposition of the noble metals in the molding. The basic solution may be brought into contact with the molding according to the invention either simultaneously with the noble metal solution or in any desired order with this solution. Where the molding according to the invention is impregnated in succession with the two solutions, intermediate drying may be performed after the first impregnation stage.

The molding according to the invention may preferably be impregnated first with the basic compound. Subsequent impregnation with the solution containing palladium and gold may result in the precipitation of a superficial shell of palladium and gold on the molding according to the invention. Reversing the order of the impregnation stages may generally result in a more or less homogeneous distribution of the noble metals over the cross-section of the molding according to the invention. However, given suitable control of the process, catalysts having a defined shell may also be obtained with the reverse order of impregnation (c.f. for example U.S. Pat. No. 4,048,096). Catalysts having a homogeneous or virtually homogeneous noble metal distribution may generally exhibit lower activity and selectivity.

Supported catalysts having shell thicknesses of less than 1 mm, preferably of less than 0.8 mm, are particularly suitable. Shell thickness may be influenced by the quantity of basic compound applied onto the support material, relative to the desired quantity of the noble metals. The greater is this ratio, the thinner is the resultant shell. The quantity ratio of basic compound to noble metal compounds required for a desired shell thickness may depend upon the nature of the support material and upon the basic compound and noble metal compounds selected. The required quantity ratio is conveniently determined by some preliminary testing. The resultant shell thickness may here simply be determined by sectioning the catalyst particles.

The minimum necessary quantity of the basic compound is determined from the stoichiometrically calculated quantity of hydroxide ions required for converting the palladium and gold into the hydroxides. A suitable guideline is that a 1- to 10-fold stoichiometric excess should be used for a shell thickness of 0.5 mm.

The moldings according to the invention may be surface-modified with the basic compounds and the noble metal salts using the pore volume impregnation process. If intermediate drying is used, the volume of the two solutions is selected such that they each correspond to approx. 90 to 100% of the absorption capacity of the moldings according to the invention. If intermediate drying is dispensed with, the sum of the individual volumes of the two impregnating solutions should fulfil the above condition, wherein the individual volumes may be in a ratio of 1:9 to 9:1 to each other. A ratio by volume of 3:7 to 7:3, in particular of 1:1, is preferably used. Water may preferably be used as the solvent in both cases. Suitable organic or aqueous/organic solvents may, however, also be used.

The reaction of the noble metal salt solution with the basic solution to yield insoluble noble metal compounds may proceed slowly and, depending upon the preparation method, is not generally complete until 1 to 24 hours have elapsed. The water-insoluble noble metal compounds are then preferably treated with reducing agents. Reduction may be performed wet, for example with aqueous hydrazine hydrate, or in the gas phase with hydrogen, ethylene, forming gas or methanol vapor. Reduction may proceed at standard temperature or elevated temperature and at standard pressure or elevated pressure, optionally also with the addition of inert gases.

Before and/or after reduction of the noble metal compounds, the chloride optionally present on the support may be removed by thorough washing. After washing, the catalyst may contain less than 500 ppm, preferably less than 200 ppm, of chloride.

The catalyst precursor obtained after the reduction may be dried and, finally, be impregnated with alkali metal acetates or alkali metal compounds which are entirely or partially converted into alkali metal acetates under the reaction conditions for the production of vinyl acetate monomer.

Impregnation may preferably be performed with potassium acetate. Pore volume impregnation may preferably be used again in this case. In other words, the required quantity of potassium acetate is dissolved in a solvent, preferably water, the volume of which approximately corresponds to the absorption capacity of the initially introduced support material for the selected solvent. This volume is approximately equal to the total pore volume of the support material.

The finished catalyst may then be dried to a residual moisture content of less than 5%. Drying may be performed in air, optionally also under nitrogen as an inert gas.

Supported catalysts of the Pd/alkali metal/Cd or Pd/alkali metal/Ba systems on the moldings according to the invention may be produced in accordance with the patents cited above.

For the purposes of vinyl acetate monomer synthesis, it is convenient to surface modify the catalyst with 0.2 to 4 wt. %, preferably 0.3 to 3 wt. % of palladium, 0.1 to 2 wt. %, preferably 0.15 to 1.5 wt. % of gold and 1 to 10 wt. %, preferably 1.5 to 9 wt. % of potassium acetate, in each case relative to the weight of the support used. These figures also apply to the Pd/alkali metal/Au system. In the case of catalyst supports having a bulk density of 500 g/l, these concentration figures correspond to volume-related concentrations of 1.0 to 20 g/l of palladium, 0.5 to 10 g/l of gold and 5 to 50 g/l of potassium acetate. The impregnating solutions may be prepared by dissolving the corresponding quantities of the palladium and gold compounds in a volume of water which corresponds to approximately 10 to 100% of the water absorption capacity of the initially introduced support material. The basic solution may be produced in an analogous manner.

The cadmium content of the Pd/alkali metal/Cd catalysts may amount to 0.1 to 2.5 wt. %, preferably 0.4 to 2.0 wt. %.

The barium content of the Pd/alkali metal/Ba catalysts may amount to 0.1 to 2.0 wt. %, preferably 0.2 to 1.8 wt. %.

The palladium content of the Pd/alkali metal/Cd or Pd/alkali metal/Ba catalysts may amount to 0.2 to 4 wt. %, preferably 0.3 to 3 wt. % of palladium.

The potassium content of the Pd/alkali metal/Cd or Pd/alkali metal/Ba catalysts may amount to 1 to 10 wt. %, preferably 1.5 to 9 wt. %.

Mixed oxides are produced by injecting volatile metal compounds into a detonating gas flame of hydrogen and air. These metal compounds hydrolyze under the action of the water generated in the detonating gas reaction to yield metal oxides and hydrochloric acid. After leaving the flame, the metal oxide enters a so-called coagulation zone, in which the mixed oxide primary particles and primary aggregates agglomerate. The product, which at this stage is in the form of a kind of aerosol, is separated from the gaseous accompanying substances in cyclones and is then post-treated with moist hot air. The residual hydrochloric acid content may be reduced to below 0.025% by this process. Since, at the end of this process, the mixed oxide is obtained with a bulk density of only approx. 15 g/l, vacuum compaction may subsequently be performed, by means of which tamped densities of approximately 50 g/l and above may be established.

The particle sizes of the products obtained in this manner may be varied by means of the reaction conditions, such as for example flame temperature, hydrogen or oxygen content, the nature and quantity of the metal chloride substances, the residence time in the flame or the length of the coagulation section.

The BET surface area is determined with nitrogen according to DIN 66 131. The pore volume is calculated from the sum of the micro-, meso- and macropore volumes. Fracture strength is determined using a model TBH 28 Erweka fracture strength tester.

Micro- and mesopores are determined by recording an $N_2$ isotherm and evaluating it in accordance with BET, de Boer and Barret, Joyner, Halenda.

Bulk density is determined in the conventional manner known to the person skilled in the art.

Macropores are determined using the Hg infiltration method.

DETAILED DESCRIPTION OF THE PREFERRED EMBODIMENTS

Examples 1–6 demonstrate, by way of example, the production of the moldings according to the invention based on pyrogenically produced mixed oxide.

EXAMPLE 1

| | |
|---|---|
| 71.4 wt. % | of pyrogenic $SiO_2/TiO_2$ mixed oxide (70 wt. % $SiO_2$, 30 wt. % $TiO_2$) |
| 12.9 wt. % | of methylhydroxyethylcellulose |
| 7.1 wt. % | of wax |
| 8.6 wt. % | of polyethylene glycol | are compacted with the addition of water, dried at 90° C., comminuted to yield a pourable powder and shaped into moldings using an eccentric press. The green tablets are calcined for 6 hours at 750° C.

EXAMPLE 2

| | |
|---|---|
| 71.4 wt. % | of pyrogenic $SiO_2/TiO_2$ mixed oxide (82 wt. % $SiO_2$, 18 wt. % $TiO_2$) |
| 12.9 wt. % | of methylhydroxyethylcellulose |
| 7.1 wt. % | of wax |
| 8.6 wt. % | of polyethylene glycol | are compacted with the addition of water, dried at 100° C., comminuted to yield a pourable powder and shaped into moldings using an eccentric press. The green tablets are calcined for 6 hours at 700° C.

EXAMPLE 3

| | |
|---|---|
| 71.4 wt. % | of pyrogenic $SiO_2/TiO_2$ mixed oxide (91 wt. % $SiO_2$, 9 wt. % $TiO_2$) |
| 12.9 wt. % | of methylhydroxyethylcellulose |
| 7.1 wt. % | of wax |
| 8.6 wt. % | of polyethylene glycol | are compacted with the addition of water, dried at 100° C., comminuted to yield a pourable powder and shaped into moldings using an eccentric press. The green tablets are calcined for 10 hours at 600° C.

EXAMPLE 4

| | |
|---|---|
| 71.4 wt. % | of pyrogenic $SiO_2/TiO_2$ mixed oxide (91 wt. % $SiO_2$, 9 wt. % $TiO_2$) |

-continued

| | |
|---|---|
| 12.9 wt. % | of methylhydroxyethylcellulose |
| 7.1 wt. % | of wax |
| 8.6 wt. % | of polyethylene glycol | are compacted with the addition of water, dried at 100° C., comminuted to yield a pourable powder and shaped into moldings using an eccentric press. The green tablets are calcined for 6 hours at 750° C.

EXAMPLE 5

| | |
|---|---|
| 90.0 wt. % | of pyrogenic $TiO_2/ZrO_2$ mixed oxide (94 wt. % $TiO_2$, 6 wt. % $ZrO_2$) |
| 5.0 wt. % | of methylhydroxyethylcellulose |
| 2.0 wt. % | of wax |
| 3.0 wt. % | of polyethylene glycol | are compacted with the addition of water, dried at 100° C., comminuted to yield a pourable powder and shaped into moldings using an eccentric press. The green tablets are calcined for 10 hours at 400° C.

EXAMPLE 6

| | |
|---|---|
| 92.6 wt. % | of pyrogenic $TiO_2/ZrO_2$ mixed oxide (94 wt. % $TiO_2$, 6 wt. % $ZrO_2$) |
| 0.9 wt. % | of methylhydroxyethylcellulose |
| 6.5 wt. % | of wax | are compacted with the addition of water, dried at 100° C., comminuted to yield a pourable powder and shaped into moldings using an eccentric press. The green tablets are calcined for 10 hours at 400° C.

The resultant moldings exhibit the following physico-chemical parameters:

end, a palladium/gold/potassium acetate catalyst was produced on a pyrogenic silica catalyst support (BET surface area 168 m²/g, bulk density 470 g/l, total pore volume 0.84 cm³/g, tablets of diameter 6 mm and height 5.5 mm, Mg content <50 micrograms/g). The concentration of the impregnating solutions was selected such that the finished catalyst contained a concentration of 0.55 wt. % palladium, 0.25 wt. % gold and 5.0 wt. % potassium acetate.

In a first stage, the support was initially impregnated with a basic solution of sodium hydroxide in water. The volume of the aqueous NaOH solution corresponded to 50% of the water absorption capacity of the dry support. After impregnation with sodium hydroxide, the support was directly impregnated without intermediate drying with an aqueous noble metal solution of sodium palladium chloride and tetrachloroauric acid, the volume of which likewise corresponded to 50% of the water absorption capacity of the dry support material.

After a waiting period of 1.5 hours for hydrolysis of the noble metal compounds, the support particles were washed free of chloride. The catalyst was dried and reduced at 450° C. in the gas phase with forming gas. The catalyst was then impregnated with an aqueous potassium acetate solution and dried again. Drying was performed in the gas phase with nitrogen.

The concentration of the basic sodium hydroxide solution was calculated such that a noble metal shell of <1.0 mm was formed on the support particles. This is catalyst A not according to the invention.

EXAMPLE 8

A Pd/Au/K catalyst was produced in the same manner as in Example 7 (comparative Example) on the basis of the molding according to Example 1. This catalyst also contained 0.55 wt. % palladium, 0.25 wt. % gold and 5.0 wt. % potassium acetate. This is catalyst B according to the invention.

EXAMPLE 9

Catalyst A not according to the invention (Example 7) and the catalyst B according to the invention (Example 8) were both tested for the production of vinyl acetate monomer (VAM).

| | Example | | | | | |
|---|---|---|---|---|---|---|
| | 1 | 2 | 3 | 4 | 5 | 6 |
| Tablet shape | Cylinders | Cylinders | Cylinders | Cylinders | Rings | Rings |
| External diameter × height × internal diameter (mm) | 5 × 5 | 6 × 5.5 | 6 × 5.5 | 5 × 5 | 8 × 5 × 3 | 8 × 5 × 3 |
| BET surface area (m²/g) | 86 | 101 | 209 | 191 | 44 | 46 |
| Pore volume (ml/g) | 0.69 | 0.59 | 0.83 | 0.72 | 0.34 | 0.42 |
| Fracture strength (N) | 21 | 34 | 37 | 66 | 15 | 12 |
| Bulk density (g/l) | n.d. | 610 | 505 | n.d. | 860 | 800 |

The following Examples illustrate the performance of the supported example according to the invention by way of example.

EXAMPLE 7

Comparative Example

A palladium/gold/potassium acetate catalyst was produced according to Example 10 of EP 0 807 615 A1. To this The activity and selectivity of the catalysts were measured for a test period of up to 24 hours.

The catalysts were tested in an oil-heated tubular-flow reactor (reactor length 710 mm, internal diameter 23.7 mm) at standard pressure and a space velocity (GHSV) of 550 h⁻¹ with the following gas composition: 75 vol. % ethylene, 16.6 vol. % acetic acid, 8.3 vol. % oxygen. The catalysts were investigated in the temperature range from 120° to 165° C., measured in the catalyst bed.

The reaction products were analyzed at the reactor outlet by means of on-line gas chromatography. Catalyst activity was measured by determining the space/time yield of the catalyst in grams of vinyl acetate monomer per hour and liter of catalyst (g VAM/(h×$l_{cat}$).

Carbon dioxide, which in particular is formed by the combustion of ethylene, was also determined and used to evaluate catalyst selectivity.

The following Table summarizes the test results. Activity and selectivity are stated as relative values, with the activity and selectivity of the catalyst not according to the invention being set at 100%. As the data clearly confirm, the catalyst B according to the invention is distinctly better than the comparison catalyst A with regard to both activity and selectivity.

| Catalyst | Relative activity on the basis of g VAM/(h × $l_{cat}$) in %* | Relative selectivity $CO_2$ in exit gas on the basis of area-% in %* | Catalyst temperature °C. |
|---|---|---|---|
| A (not according to the invention) | 100 | 100 | 162.5 |
| B (according to the invention) | 111.2 | 82.7 | 164.2 |

*see description for definition.

What is claimed is:

1. A supported catalyst comprising:

at least one member selected from the group consisting of palladium and palladium compounds;

at least one alkali metal compound; and at least one member selected from the group consisting of gold, gold compounds, cadmium, cadmium compounds, barium, barium compounds, and mixtures of at least two members selected from the group consisting of gold, cadmium and barium, as the catalytically active component on a support molding, wherein the support molding comprises a pyrogenically produced mixed oxide having the following physicochemical parameters:

| | |
|---|---|
| External diameter | 0.8–25 mm |
| BET surface area | 5–400 m²/g |
| Pore volume | 0.2–1.8 ml/g |
| Fracture strength | 5–350 N |
| Composition | at least two members selected from the group consisting of $SiO_2$, $Al_2O_3$, $TiO_2$ and $ZrO_2$ in any desired combination but with the exception of $SiO_2/Al_2O_3$ mixed oxides, in which >75 wt. % of $SiO_2$ is present |
| Other constituents | <1 wt. % |
| Bulk density | 250–1500 g/l. |

2. The supported catalyst according to claim 1, wherein a Pd/K/Au system is used as the catalytically active component.

3. The supported catalyst according to claim 2, wherein the alkali metal compound comprises potassium acetate.

4. The supported catalyst according to claim 1, wherein the alkali metal compound comprises potassium acetate.

5. A process for producing the supported catalyst according to claim 1, comprising:

applying one or more of the Pd, Au, Cd, and Ba metal compounds to the support molding by impregnation, spraying, vapor deposition, immersion or precipitation;

washing to remove any optionally present chloride content;

optionally, before or after the washing, reducing the reducible metal compounds applied to the support molding; and impregnating with alkali metal acetates or alkali metal compounds which are at least partially converted into alkali metal acetates under reaction conditions for production of vinyl acetate monomer.

6. The process according to claim 5, wherein the alkali metal acetate or the alkali metal compound comprises potassium acetate.

7. A process for producing the supported catalyst according to claim 1, comprising:

impregnating the support molding with (a) a basic solution and (b) a solution containing gold and palladium salts, wherein impregnation with (a) and (b) proceeds simultaneously or successively, optionally with intermediate drying, wherein solution (a) contains one or more alkali compounds and solution (b) contains one or more of the Pd, Au, Cd, and Ba metal compounds;

washing the support molding to remove any optionally present chloride content;

before or after the washing, reducing the insoluble compounds precipitated on the support;

drying the resultant catalyst precursor, and impregnating the resultant catalyst precursor with alkali metal acetates or alkali metal compounds which are at least partially converted into alkali metal acetates under reaction conditions for the production of vinyl acetate monomer.

8. The process according to claim 7, wherein the alkali metal acetate or the alkali metal compound comprises potassium acetate.

* * * * *